United States Patent [19]

Barton et al.

[11] 4,257,801

[45] Mar. 24, 1981

[54] COTTON DESICCATION WITH PHENOXYALKANOIC ACIDS

[75] Inventors: John E. D. Barton, Wokingham; Donald W. R. Headford, Reading; David J. Collins, Crowthorne, all of England

[73] Assignee: Imperial Chemical Industries Limited, London, England

[21] Appl. No.: 77,339

[22] Filed: Sep. 20, 1979

Related U.S. Application Data

[63] Continuation of Ser. No. 881,065, Feb. 24, 1978, abandoned.

[30] Foreign Application Priority Data

Mar. 9, 1977 [GB] United Kingdom ................. 9878/77

[51] Int. Cl.³ ............................................. A01N 37/40
[52] U.S. Cl. ........................................ 71/70; 71/108

[58] Field of Search ..................... 71/70, 108

[56] References Cited

U.S. PATENT DOCUMENTS

| | | | |
|---|---|---|---|
| 3,457,062 | 7/1969 | Young ................................. | 71/70 |
| 4,013,451 | 3/1977 | Poignant et al. .................. | 71/108 X |
| 4,051,184 | 9/1977 | Areklev et al. .................... | 71/70 X |

OTHER PUBLICATIONS

Aberg. Chem. Abst. vol. 75 (1971), 108899m.
Martin et al. Chem. Abst. vol. 80 (1974), 104770w.

Primary Examiner—Catherine L. Mills
Attorney, Agent, or Firm—Cushman, Darby & Cushman

[57] ABSTRACT

A method of dessicating growing cotton plants employing 2, 5-dichlorophenoxy propionic acid and derivatives thereof.

5 Claims, No Drawings

COTTON DESICCATION WITH PHENOXYALKANOIC ACIDS

This is a continuation of application Ser. No. 881,065 filed Feb. 24, 1978, now abandoned.

This invention relates to the desiccation of cotton plants.

In the mechanical harvesting of cotton crops, the presence of green leaves and stems on the cotton plants is disadvantageous, since the leaves and stems tend to be crushed during the harvesting operation, and to leave green stains on the cotton. Accordingly it is general practice to spray the crop, at a convenient interval before harvesting, with a chemical desiccant in order to dry up the green leaves and stems.

A certain class of chlorinated phenoxypropionic acid derivatives has now unexpectedly been found to be useful for this purpose.

According to the present invention, there is provided a process of desiccating growing cotton plants, which comprises applying to the foliage of the plants a phenoxypropionic acid derivative of the following formula (I):

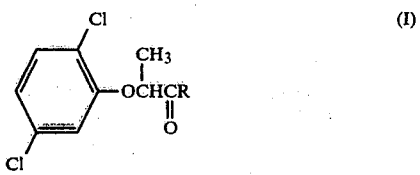

wherein R is an —OH group, an OM group wherein M is a cation; a phenoxy group optionally substituted by one or more halogen atoms or alkyl groups of 1 to 4 carbon atoms; a cycloalkoxy group; an alkoxy group optionally substituted by one or more chlorine atoms, hydroxy groups, alkoxy groups, alpha (2,5-dichlorophenoxy)propionyloxy groups, dialkylamino groups, or phenyl groups optionally substituted by one or more chlorine atoms, phenoxy groups, or methyl groups; an alkenyloxy group; an alkylthio group optionally substituted by one or more phenyl groups optionally substituted by methyl or chlorine; an alkenylthio group; or a group =NR$^1$R$^2$ wherein R$^1$ represents a hydrogen atom, an alkoxy radical, an alkyl radical, an alkenyl radical, a phenyl radical, a monoalkylamino radical, or a dialkylamino radical, and R$^2$ represents a hydrogen atom, an alkyl radical, or an alkenyl radical, or R$^1$ and R$^2$, together with the nitrogen atom to which they are attached, form a pyrrolidine or piperidine ring.

When M is a cation it may be for example an alkali metal or an alkaline earth metal cation, for example a sodium, potassium, calcium, or magnesium cation. M may also be, for example an ammonium cation or a mono-, di-, tri- or tetra-substituted ammonium cation in which the substituents may be, for example, aliphatic radicals of 1 to 6 carbon atoms; these may be for example alkyl radicals of 1 to 6 carbon atoms. When R is a phenoxy group substituted by one or more halogen atoms, the halogen atoms may be fluorine, chlorine, bromine, or iodine.

When R is an alkoxy group, it may be for example an alkoxy group of 1 to 20 or more carbon atoms. Examples of alkoxy radicals within this range include those having from 1 to 12 carbon atoms, for example methoxy, ethoxy, propoxy, isopropoxy, butoxy, pentyloxy, hexyloxy, cyclohexyloxy, octyloxy, and dodecyloxy. When R is a substituted alkoxy radical it may be for example a benzyloxy radical, or a benzyloxy radical substituted by one or more chlorine atoms or methyl groups, for example a 2-chlorobenzyloxy, 3-chlorobenzyloxy, 4-chlorobenzyloxy, 2,4-dichlorobenzyloxy, or 4-methylbenzyloxy radical. Further examples of substituted alkoxy radicals include alkoxy radicals substituted by one or more hydroxy groups, alkoxy groups (for example alkoxy groups of 1 to 4 carbon atoms), chlorine atoms, dialkylamino groups, or alpha(2,5-dichlorophenoxy)propionyloxy groups. The group R may thus be, for example, a 2-hydroxyethoxy, 2-chloroethoxy, 2-diethylaminoethoxy, 2-ethoxyethoxy, 2-butoxyethoxy, or 2[alpha(2,5-dichlorophenoxy)propionyloxy]ethoxy radical.

When R is an alkenyloxy radical it may be an alkenyloxy radical of 3 to 20 carbon atoms, for example from 3 to 12 carbon atoms. Particular examples of alkenyloxy radicals within this range include allyloxy and octadecenyloxy radicals.

Examples of alkylthio radicals include those having from 1 to 12 or more carbon atoms, for example methylthio and ethylthio radicals. Examples of substituted alkylthio radicals include the benzylthio radical and benzylthio radicals substituted in the phenyl ring with one or more methyl groups or chlorine atoms, for example the 2-chlorobenzylthio, 3-chlorobenzylthio, 4-chlorobenzylthio, and 4-methylbenzylthio radicals.

Examples of alkenylthio radicals include those of 3 to 12 carbon atoms, for example the allylthio radical.

When R$^1$ is an alkoxy radical it may be for example an alkoxy radical of 1 to 4 carbon atoms, for example a methoxy radical. When R$^1$ is an alkyl radical it may be for example a methyl, ethyl, propyl, or butyl radical. When R$^1$ is an alkenyl radical it may be for example an allyl or but-2-enyl radical. When R$^1$ is a monoalkylamino or a dialkylamino radical, the alkyl groups in these radicals may each contain for example from 1 to 4 carbon atoms. When R$^2$ is an alkyl radical it may, for example contain from 1 to 4 or more carbon atoms. When R$^2$ is an alkenyl radical it may be for example an allyl or but-2-enyl radical.

Particular examples of compounds useful in the process of the invention are listed in Table I below:

TABLE I

| COMPOUND NO | R | PHYSICAL CONSTANT |
|---|---|---|
| 1 | . OH | m.p. 146° |
| 2 | . OC$_2$H$_5$ | b.p. 97–99°/0.1 Torr |
| 3 | . OCH(CH$_3$)$_2$ | b.p. 120°/0.2 Torr |
| 4 | . O—⟨⟩ | b.p. 142–145°/0.2 Torr |
| 5 | . OC$_8$H$_{17}$ | b.p. 150–155°/0.25 Torr |
| 6 | . OCH$_2$CH=CH$_2$ | b.p. 124–127°/0.2 Torr |
| 7 | . OCH$_2$C$_6$H$_5$ | m.p. 56–58° |
| 8 | —NH$_2$ | m.p. 149° |
| 9 | —NHCH$_3$ | m.p. 149° |
| 10 | —NHCH$_2$CH=CH$_2$ | m.p. 104–107° |

TABLE I-continued

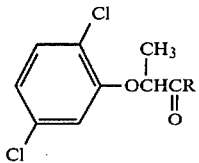

| COMPOUND NO | R | PHYSICAL CONSTANT |
|---|---|---|
| 11 | NHC$_6$H$_5$ | m.p. 123–125° |
| 12 | —NHN(CH$_3$)$_2$ | m.p. 158° |
| 13 | —N(CH$_3$)$_2$ | m.p. 86–87° |
| 14 | —N(CH$_3$)(OCH$_3$) | m.p. 59° |
| 15 | —N(C$_2$H$_5$)$_2$ | m.p. 55–57° |
| 16 | —N(C$_3$H$_7$)$_2$ | m.p. 62–64° |
| 17 | —N(CH$_2$CH=CH$_2$)$_2$ | b.p. 160–180°/0.2 Torr |
| 18 | —N(pyrrolidinyl) | m.p. 102° |
| 19 | —N(azetidinyl) | m.p. 78–80° |
| 20 | —OCH$_2$.C$_6$H$_4$.Clp | m.p. 40–42° |
| 21 | —OCH$_2$.C$_6$H$_4$.CH$_3$p | b.p. 180°/0.3 Torr |
| 22 | .OC$_{18}$H$_{37}$ | b.p. 200°/0.2 Torr |
| 23 | .OCH$_2$C$_6$H$_4$.OPhm | b.p. 230°/0.2 Torr |
| 24 | .OC$_{13}$H$_{27}$ | b.p. 220°/0.2 Torr |
| 25 | .OCH$_2$(CH$_2$)$_7$CH=CH(CH$_2$)$_7$CH$_3$ | b.p. 180°/0.2 Torr |
| 26 | .O—C$_6$H$_4$—C(CH$_3$)$_3$ | b.p. 230°/0.2 Torr |
| 27 | .OCH$_2$CH$_2$N(CH$_3$)$_2$ | b.p. 140°/0.2 Torr |
| 28 | .OCH$_2$CH$_2$O. | m.p. 130–132° |
| 29 | .OCH$_2$CH$_2$OC$_2$H$_5$ | b.p. 190° C./0.2 Torr |
| 30 | .SCH$_2$C$_6$H$_4$.Clp | b.p. 250°/0.4 Torr |

The phenoxypropionic acid derivatives may, if desired, be applied in admixture with other herbicides to desiccate cotton. Examples of herbicides which may be mixed with the phenoxypropionic derivatives for this purpose include salts of the bipyridylium herbicides paraquat and diquat. Paraquat is the accepted common name for the 1,1′-dimethyl-4,4′-bipyridylium cation, having the structural formula (II). Diquat is the accepted common name for the 1,1′-ethylene-2,2′-bipyridylium cation, having the structural formula (II):

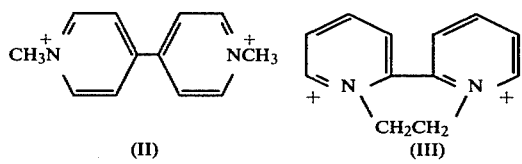

The particular salt of paraquat or diquat to be used is not critical. Conveniently the salt is one which is readily soluble in water. Examples of paraquat salts include the chloride, bromide, iodide, methylsulphate, sulphate, methylphosphate, and phosphate. Examples of diquat salts include the chloride, bromide, iodide, methylsulphate, sulphate, phosphate and p-toluenesulphonate. Since the characteristic herbicidal activity of salts of paraquat and diquat resides in the paraquat or diquat cation only, it is customary to quote concentrations of active ingredient and rates of application in terms of the amount of paraquat cation or diquat cation used, thus avoiding the inconvenience of having to quote different application rates for different salts of paraquat or diquat. Application rates and concentrations quoted in this specification therefore relate to the amount of paraquat or diquat cation unless otherwise stated.

The rate at which the phenoxypropionic acid derivatives are applied to desiccate cotton will depend upon a variety of factors, for example the identity of the particular compound chosen for use, but in general the rate will be in the range from 0.06 to 1.0 kilogram per hectare and often in the range 0.1 to 0.5 kilograms per hectare. When applied in admixture with paraquat or diquat, the amount of phenoxypropionic acid derivative can be correspondingly reduced; usually up to half or more of the weight of phenoxypropionic acid derivative can be replaced by the same weight of paraquat or diquat. Thus, instead of using 0.5 kilograms per hectare of phenoxypropionic acid derivative, a mixture of phenoxypropionic acid derivative and paraquat could be applied, each at a rate of 0.25 kilograms per hectare. An advantage of using a mixture of phenoxypropionic acid derivative and paraquat or diquat is that the desiccation process is more rapid than when the propionic acid derivative is used alone.

The phenoxypropionic acid derivatives are preferably applied in the form of compositions, in which the active ingredient is mixed with a carrier comprising a solid or liquid diluent. Preferably, a surface-active agent is also present. Conveniently, the phenoxypropionic acid derivatives are applied in the form of a solution of dispersion in water, together with a surface-active agent. When applied together with paraquat or diquat, the spray composition may comprise a solution of the phenoxypropionic acid derivative in a water-immiscible organic solvent which has been emulsified with an aqueous solution of paraquat or diquat, the mixture containing a surface-active agent to assist in its emulsification. Examples of water-immiscible organic solvents include hydrocarbon solvents, for example alkylsubstituted benzenes, and chlorinated hydrocarbons, for example ethylene dichloride.

The compounds are preferably applied in the form of compositions, in which the active ingredient is mixed with a carrier comprising a solid or liquid diluent. Preferably a surface-active agent is also present. Conveniently, the compounds are applied in the form of a solution or dispersion in water, together with a surface-active agent.

Surface active agents may be of the cationic, anionic or non-ionic type. Suitable agents of the cationic type include for example quaternary ammonium compounds, for example cetyltrimethyl ammonium bromide. Suitable agents of the anionic type include for example soaps, salts of aliphatic monoesters of sulphuric acid, for example sodium lauryl sulphate; and salts of sulphonated aromatic compounds, for example dodecylbenzenesulphonate, sodium, calcium and ammonium lignosulphonate, butylnaphthalene sulphonate, and a mixture of the sodium salts of diisopropyl- and triisopropylnaphthalenesulphonic acid. Suitable agents of the non-ionic type include, for example, the condensation products of ethylene oxide with fatty alcohols such as oleyl alcohol and cetyl alcohol, or with alkyl phenols such as octylphenol, nonylphenol, and octylcresol. Other non-ionic agents are the partial esters derived from long chain fatty acids and hexitol anhydrides, for example sorbitol monolaurate; the condensation products of the said partial esters with ethylene oxide and the lecithins. When preparing compositions containing paraquat or diquat, anionic surface-active agents are generally to be avoided since they may interact unfavourably with these cationic herbicides.

For convenience in transport, storage, and sale, concentrated compositions may be prepared, containing a high proportion of active ingredient, for example from 10 to 85% and preferably from 25 to 60% by weight of active ingredient. These concentrates are diluted with water before use.

The phenoxypropionic acid compounds used in the invention are in general known, although certain compounds are new and form a further feature of the invention. The compounds may be made by conventional methods known in the art. Thus compounds in which R is an alkoxy or alkenyloxy radical may be made from the known propionic acid derivative of the following formula:

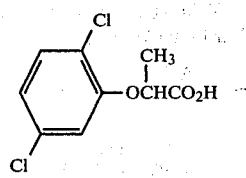

(IV)

by esterifying the acid with the appropriate alkanol or alkenol ROH to provide the required radical R. Similarly, compounds in which R represents a radical $-NR^1R^2$ may be prepared by converting the acid (IV) to the acid chloride (V) and

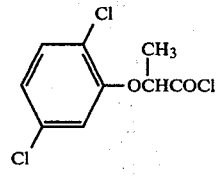

(V)

reacting (V) with the appropriate amine $HNR^1R^2$ according to conventional procedures.

The compounds which are new and which form a further part of the invention are those of the foregoing formula (I) in which the group R is a benzyloxy or benzylthio group, the phenyl moiety of which may optionally be substituted with one or more chlorine atoms or methyl groups. The compound (I) wherein the group R is an unsubstituted benzyloxy group is a particularly effective desiccant for cotton.

The invention is illustrated by the following Examples, in which all temperatures are in degrees Centigrade and all parts are by weight unless otherwise specified.

EXAMPLE 1

This Example illustrates the effect of the 2,5-dichlorophenoxy compounds used in the process of the invention for desiccating cotton, in comparison with the effect of the well known herbicide 2,4-D as its sodium salt, and in comparison with the effect of the well known herbicide paraquat.

Cotton plants, 12 weeks old, grown in the glass-house in 3-inch pots, having woody stem bases, eight true leaves, and two flower buds were sprayed with aqueous solutions or dispersions of the compounds to be tested. Three replicates were used for each treatment. The spray volume was equivalent to 200 liters per hectare. Each compound was formulated as an aqueous dispersion or solution containing 10% by volume of a solution comprising 21.8 grams per liter of Span 80 and 78.2 grams per liter of Tween 20 in methylcyclohexanone. Span 80 is a Trade mark for a surfactant comprising sorbitan monolaurate and Tween 20 is a Trade Mark for a surfactant comprising sorbitan monolaurate condensed with 20 molar proportions of ethylene oxide.

Visual assessments of the percentage kill of the cotton plants were made at intervals after spraying. The results are given in Table II below:

TABLE II

| COMPOUND | RATE OF APPLICATION kg/ha | PERCENTAGE KILL, DAYS AFTER SPRAYING | | | | |
|---|---|---|---|---|---|---|
| | | 1 DAY | 3 DAYS | 8 DAYS | 14 DAYS | 21 DAYS |
| 1 | 0.33 | 0 | 7 | 48 | 83 | 90 |
| 1 | 1 | 3 | 10 | 62 | 93 | 95 |
| 1 | 3.0 | 17 | 17 | 72 | 95 | 100 |
| 2 | 0.33 | 5 | 13 | 83 | 95 | 95 |
| 2 | 1 | 13 | 13 | 80 | 93 | 97 |
| 2 | 3.0 | 17 | 28 | 80 | 97 | 99 |
| 2,4-D | 0.33 | 0 | 0 | 30 | 60 | 83 |
| 2,4-D | 1 | 0 | 2 | 35 | 62 | 82 |
| 2,4-D | 3.0 | 0 | 8 | 38 | 65 | 82 |
| PQ | 0.33 | 33 | 55 | 73 | 82 | 72 |
| PQ | 1 | 53 | 75 | 82 | 83 | 77 |
| PQ | 3.0 | 80 | 88 | 93 | 100 | 100 |
| Control | — | 0 | 0 | 0 | 0 | 0 |

In the above Table, PQ stands for paraquat, used as its dichloride; this herbicide is used commercially for cotton desiccation. The paraquat treatments gave rapid initial leaf desiccation but regrowth from the apex and from basal axillary buds produced further leaves at doses below 3 kilograms per hectare; accordingly the final score at the lower rates of application was lower than at the penultimate assessment. The 2,4-D treatments were very slow to act, and gave incomplete leaf kill even at 21 days. The compounds no. 1 and 2 were intermediate in speed of desiccation. By 14 days they had both given very good kill of the tops, and there was no green regrowth, which is often observed with proprietary desiccants under practical conditions in the field.

EXAMPLE 2

This Example illustrates the selective effect of compound no. 1 in inducing desiccation in cotton. The compound was formulated for test by mixing an appropriate amount of the compound with 5 ml of an emulsion prepared by diluting 160 ml of a solution containing 21.8 grams per liter of Span 80 and 78.2 grams per liter of Tween 20 in methylcyclohexanone to 500 ml with water. The mixture of the compound and the emulsion was shaken with glass beads and diluted to 40 ml with water.

The spray composition so prepared was sprayed on to young pot plants of the species named in Table III below at a rate equivalent to 1000 liters per hectare (1 kilogram per hectare). The damage to the plants was assessed after two weeks, on a scale of 0 to 5 where 0 is no effect and 5 is complete kill. The results are given in Table III below:

TABLE III

| | | | | | | | TEST PLANTS | | | | | | | | | | | | | | |
|---|---|---|---|---|---|---|---|---|---|---|---|---|---|---|---|---|---|---|---|---|---|
| Sb | Rp | Ct | Sy | Mz | Wh | Rc | Sn | Ip | Am | Pi | Ca | Po | Xa | Ab | Ot | Dg | Pn | St | Ec | Sh | Ag | Cn |
| 2 | 1 | 5 | 1 | 0 | 0 | 0 | 0 | 4 | 1 | 1 | 4 | 2 | 2 | 1 | 0 | 2 | 1 | 2 | 0 | 1 | 0 | 1 |

Test plants

| | | | | | | |
|---|---|---|---|---|---|---|
| Sb | Sugar beet | Ip | *Ipomoea purpurea* | Dg | *Digitaria sanguinalis* |
| Rp | Rape | Am | *Amaranthus retroflexus* | Pn | *Poa annua* |
| Ct | Cotton | Pi | *Polygonum aviculare* | St | *Setaria viridis* |
| Sy | Soyabean | Ca | *Chenopodium album* | Ec | *Echinochloa crus-galli* |
| Mz | Maize | Po | *Portulaca oleracea* | Sh | *Sorghum halepense* |
| Wh | Wheat | Xa | *Xanthium pennsylvanicum* | Ag | *Agropyron repens* |
| Rc | Rice | Ab | *Abutilon theophrastii* | Cn | *Cyperus rotundus* |
| Sn | *Senecio vulgaris* | Ot | *Avena fatua* | | |

From the results in Table III it can be seen that only in the case of cotton was complete kill observed at the rate of application employed in this test.

EXAMPLE 3

This Example illustrates the cotton-desiccating effect of mixtures of paraquat with compounds no 13 and 2. Tests were carried out with these mixtures according to the procedure described in Example 1. The paraquat used was in the form of its dichloride salt. Percentage kill of cotton plants (the average value for 3 replicates) was assessed visually at intervals after treatment. The following tables give the results of the tests.

TABLE IV

| | DAYS AFTER TREATMENT | | | | |
|---|---|---|---|---|---|
| TREATMENT | 1 | 3 | 7 | 14 | 21 |
| Compound 13 (0.25 kg/ha) | 0 | 0 | 25 | 35 | 55 |
| Paraquat (0.25 kg/ha) | 60 | 70 | 75 | 75 | 65 |
| Mixture of paraquat (0.25 kg/ha and compound 13 (0.25 kg/ha) | 55 | 80 | 85 | 90 | 85 |
| Expected effect from mixture | 60 | 70 | 81 | 84 | 84 |

TABLE V

| | DAYS AFTER TREATMENT | | | | |
|---|---|---|---|---|---|
| TREATMENT | 1 | 3 | 7 | 14 | 21 |
| Compound 2 (0.25 kg/ha) | 0 | 20 | 45 | 45 | 60 |
| Paraquat (0.25 kg/ha) | 60 | 70 | 75 | 75 | 65 |
| Mixture of compound 2 (0.25 kg/ha and paraquat (0.25 kg/ha) | 85 | 90 | 100 | 100 | 95 |
| Expected effect from mixture | 60 | 76 | 86 | 86 | 86 |

In the above tables, the figures opposite the heading "Expected effect from mixture" are calculated from the effects of the two components of the mixture applied separately, using the formula:-

$$E = P + \frac{(100 - P)C}{100}$$

wherein E is the expected effect, P is the percentage kill caused by paraquat and C is the percentage kill caused by the test compound.

It will be noted that in the above tables the observed effect of the mixture of paraquat and test compound was in most cases greater than the expected effect; that is to say, the mixtures showed a synergistic effect. The mixtures gave a rapid kill of the foliage with very little production of new leaves. Paraquat on its own gave a rapid desiccation of the foliage but regrowth was observed from the apex and the axillary buds on the stem.

EXAMPLE 4

Following the test procedures described in Examples 1 and 3, further compounds listed in Table I were tested for their ability to desiccate cotton, alone or in admixture with paraquat (PQ) as its dichloride salt. The results are given in Table VI below.

TABLE VI

| COMPOUND NO | RATE OF APPLICATION kg/ha | PERCENTAGE DESICCATION 28 DAYS AFTER SPRAYING |
|---|---|---|
| 2 | 0.25 | 77 |
| 2 | 1.0 | 99 |
| 4 | 0.25 | 88 |
| 4 | 1.0 | 99 |
| 5 | 0.25 | 99 |
| 5 | 1.0 | 99 |
| 7 | 0.25 | 99 |
| 7 | 1.0 | 99 |
| 14 | 0.25 | 55 |
| 14 | 1.0 | 77 |
| 16 | 0.25 | 77 |
| 16 | 1.0 | 88 |
| 18 | 0.25 | 88 |
| 18 | 1.0 | 88 |
| PQ | 0.25 | 77 |
| PQ | 1.0 | 99 |
| PQ + Compound 2 | 0.25 + 0.25 | 88 |
| PQ + Compound 4 | 0.25 + 0.25 | 66 |
| PQ + Compound 5 | 0.25 + 0.25 | 88 |
| PQ + Compound 7 | 0.25 + 0.25 | 99 |
| PQ + Compound 14 | 0.25 + 0.25 | 66 |
| PQ + Compound 16 | 0.25 + 0.25 | 66 |
| PQ + Compound 18 | 0.25 + 0.25 | 88 |
| Control (unsprayed) | — | 0 |

EXAMPLE 5

This Example illustrates the cotton-desiccating activity of compounds used in the process of the invention, alone and in admixture with paraquat (PQ) in the form of its dichloride salt.

Two field trials were carried out in Spain on cotton. The cotton plants were sprayed with aqueous dispersions of the compounds and percentage desiccation was assessed after the lapse of a period of time specified in the tables below. Results are given in the following tables.

| RESULTS OF FIELD TRIAL 1 | | |
|---|---|---|
| COMPOUND NO | RATE OF APPLICATION kg/ha | PERCENTAGE DESICCATION 14 DAYS AFTER APPLICATION |
| Compound 13 | 0.5 | 28 |
|  | 1.0 | 43 |
|  | 2.0 | 58 |
| Compound 13 + PQ | 0.5 + 0.25 | 48 |
| Compound 13 + PQ | 1.0 + 0.25 | 53 |
| Compound 2 | 0.5 | 60 |
|  | 1.0 | 75 |
|  | 2.0 | 89 |
| Compound 2 + PQ | 0.5 + 0.25 | 73 |
| Compound 2 + PQ | 1.0 + 0.25 | 53 |
| PQ | 0.25 | 9 |
| PQ | 0.5 | 20 |
| Control (unsprayed) | — | 0 |

| RESULTS OF FIELD TRIAL 2 | | |
|---|---|---|
| COMPOUND NO | RATE OF APPLICATION kg/ha | PERCENTAGE DESICCATION 15 DAYS AFTER APPLICATION |
| Compound 13 | 0.5 | 68 |
|  | 1.0 | 88 |
|  | 2.0 | 98 |
| Compound 13 + PQ | 0.5 + 0.25 | 90 |
| Compound 13 + PQ | 1.0 + 0.25 | 93 |
| Compound 2 | 0.5 | 95 |
|  | 1.0 | 100 |
|  | 2.0 | 100 |
| Compound 2 + PQ | 0.5 + 0.25 | 95 |
| Compound 2 + PQ | 1.0 + 0.25 | 100 |
| PQ | 0.25 | 70 |
| PQ | 0.5 | 85 |
| Control (unsprayed) | — | 0 |

EXAMPLE 6

This Example illustrates the preparation of esters of alpha (2,5-dichlorophenoxy)propionic acid by means of a description of the preparation of ethyl alpha(2,5-dichlorophenoxy)propionate.

2,5-Dichlorophenol (8.2 g), anhydrous potassium carbonate (6.9 g), and ethyl alpha-bromopropionate (9.05 g) were heated under reflux in methyl ethyl ketone (100 ml) for 2 hours. The mixture was cooled and the solvent removed under reduced pressure. The residue was diluted with water and extracted with dichloromethane. The extracts were dried and evaporated to give an oil. Distillation of the oil gave the required ethyl ester (Compound no 2), with a boiling point of 97°–99° C./0.1 Torr.

EXAMPLE 7

This Example illustrates the preparation of amides of alpha (2,5-dichlorophenoxy)propionic acid by means of a description of the preparation of N,N-dimethyl-alpha(2,5-dichlorophenoxy)propionamide (compound no 13).

(a) Preparation of alpha (2,5-dichlorophenoxy)propionyl chloride.

Thionyl chloride (23.8 g) was added to a stirred solution of alpha(2,5-dichlorophenoxy)propionic acid (17.5 g) in dry toluene (100 ml). The mixture was heated under reflux for 2 hours and then left to cool overnight. The solvent was removed under reduced pressure and the remaining acid chloride used without further purification.

(b) Preparation of amide.

A solution of the acid chloride (78 g) from (a) in ether (50 ml) was added with stirring to a solution of dimethylamine (45 g) in water (200 ml) covered with a layer of ether (200 ml), and cooled to 0°–5° C., keeping the reaction temperature below 15° C. during the addition. On completion of the addition, the reaction mixture was stirred for a further 2 hours at room temperature. The aqueous layer was separated and extracted with ether. The ethereal extract was combined with the original ether layer, dried, and evaporated to give a white solid. Recrystallization from petroleum (b.p. 80°–100° C.) gave the amide with a melting point of 86°–87° C.

EXAMPLE 8

This Example illustrates a method of preparing esters of alpha(2,5-dichlorophenoxy)propionic acid alternative to that described in Example 1.

The acid chloride (4 g) prepared as in paragraph (a) of Example 6, dissolved in ether (5 ml) was added to a solution of triethylamine (1.6 g) in benzyl alcohol (25 ml), at an initial temperature of 10° C., keeping the temperature below 20° C. during the addition. After stirring for 1 hour at 15° C. the temperature was raised to 60° C. for 2 hours. The mixture was then cooled and distilled under reduced pressure. After the excess of benzyl alcohol had been removed, a distillate was obtained which solidified. Recrystallisation of this solid from ethanol gave benzyl alpha(2,5-dichlorophenoxy)-propionate (compound no 7 of Table I) with a melting point of 56°–58° C.

I claim:

1. A process of desiccating growing cotton plants, which comprises applying to the foliage of the plants an effective amount of a phenoxypropionic acid derivative of the following formula (I):

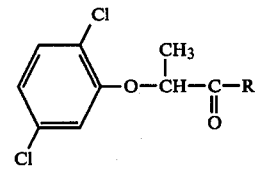

wherein R is an —OH group; an OM group wherein M is an alkali metal, alkaline earth metal, ammonium or mono-, di-, tri- or tetra-($C_{1-6}$ alkyl) substituted ammonium cation; a phenoxy group optionally substituted by one or more halogen atoms or $C_{1-4}$ alkyl groups; a cyclohexyloxy group; a $C_{1-12}$ alkoxy group optionally substituted by one or more chlorine atoms, hydroxy groups, $C_{1-4}$ alkoxy groups, alpha(2,5-dichlorophenoxy)propionyloxy, dialkylamino or phenyl groups optionally substituted by one or more chlorine atoms, phenoxy groups, or methyl groups; a $C_{3-12}$ alkenyloxy group; a $C_{1-12}$ alkylthio group optionally substituted by one or more phenyl groups which are unsubstituted or substituted by methyl or chlorine; a $C_{3-12}$ alkenylthio group; or a group -$NR^1R^2$ wherein $R^1$ represents a hydrogen atom, a $C_{1-4}$ alkoxy radical, a $C_{1-4}$ alkyl radical, an allyl radical, a but-2-enyl radical, a phenyl radical, a mono($C_{1-4}$alkyl)amino radical, or a di($C_{1-4}$alkyl)amino radical; and $R^2$ represents a hydrogen atom, a $C_{1-4}$ alkyl radical, an allyl or a but-2-enyl radical; or $R^1$ and $R^2$, together with the nitrogen atom to which they are attached, form a pyrrolidine or piperidine ring.

2. A process as claimed in claim 1, wherein R is a $C_{1-12}$ alkoxy group optionally substituted by one or more chlorine atoms, hydroxy groups, $C_{1-4}$ alkoxy groups, alpha(2,5-dichlorophenoxy)-propionyloxy groups, or phenyl groups optionally substituted by one or more chlorine atoms or methyl groups.

3. A process as claimed in claim 1, wherein R is a benzyloxy radical, or a benzyloxy radical substituted with one or more chlorine atoms or methyl groups.

4. A process as claimed in claim 1 wherein the rate of application of the phenoxypropionic acid derivative is from 0.06 to 1.0 kilograms per hectare.

5. A process as claimed in claim 1 wherein the propionic acid derivative is the one in which R is a benzyloxy radical.

* * * * *